United States Patent
Govari et al.

(10) Patent No.: US 6,638,231 B2
(45) Date of Patent: Oct. 28, 2003

(54) IMPLANTABLE TELEMETRIC MEDICAL SENSOR AND METHOD

(75) Inventors: Assaf Govari, Haifa (IL); Shlomo Ben-Haim, Haifa (IL); Joel Zilberstein, Haifa (IL); Louis J. Capezzuto, Monroe, NJ (US)

(73) Assignee: Biosense, Inc., New Brunswick, NJ (US)

( * ) Notice: Subject to any disclaimer, the term of this patent is extended or adjusted under 35 U.S.C. 154(b) by 222 days.

(21) Appl. No.: 09/739,053

(22) Filed: Dec. 18, 2000

(65) Prior Publication Data

US 2002/0077553 A1 Jun. 20, 2002

(51) Int. Cl.$^7$ ................................................ A61B 5/02
(52) U.S. Cl. ..................... 600/486; 600/485; 600/301; 600/561; 128/903; 128/899
(58) Field of Search ............................... 600/483, 484, 600/485, 486, 487, 488, 300, 317, 301, 509, 561, 505, 462, 480; 607/2, 9, 18, 27; 128/903, 899

(56) References Cited

U.S. PATENT DOCUMENTS

| 3,672,352 A | 6/1972 | Summers |
| 4,114,151 A | 9/1978 | Denne et al. |
| 4,198,987 A | 4/1980 | Cain et al. |
| RE30,366 E | 8/1980 | Rasor et al. |
| 4,262,632 A | 4/1981 | Hanton et al. |

(List continued on next page.)

FOREIGN PATENT DOCUMENTS

| DE | 30 11 671 A1 | 10/1981 |
| DE | 3219558 A1 | 12/1983 |
| DE | 299 09 923 U1 | 10/1999 |
| EP | 0 021 451 A1 | 7/1981 |
| EP | 0 053 976 A2 | 6/1982 |

(List continued on next page.)

OTHER PUBLICATIONS

European Search Report EP 01 31 0521 dated Mar. 19, 2002.
Dargie, Henry J. "Diagnosis and Management of Heart Failure", BMJ 1994;308:321–8.
Stevenson, LW & Perloff, JK "The Limited Reliability of Physical Signs for Estimating Hemodynamics in Chronic Heart Failure", JAMA 1989;261, No.6:884–888.
Chakko S et al. "Clinical, Radiographic, and Hemodynamic Correlations in Chronic Congestive Heart Failure: Conflicting Results May Lead to Inappropriate Care", AJM 1991;90:353–359.
Stevenson LW "Tailored Therapy Before Transplantation for Treatment of Advanced Heart Failure: Effective Use of Vasodilators and Diuretics", J Heart Lung Transplant 1991;10:468–76.
Stevenson LW et al. "Poor Survival of Patients with Idopathic Cardiomyopathy Considered Too Well for Transplantation", AJM 1987;83:871–876.

(List continued on next page.)

Primary Examiner—Teresa Walberg
Assistant Examiner—Fadi H. Dahbour
(74) Attorney, Agent, or Firm—Louis J. Capezzuto

(57) ABSTRACT

A telemetric medical sensor for implantation in a patient's body for measuring a parameter therein is provided. The sensor comprises a housing and a membrane at one end of the housing. The membrane is deformable in response to the parameter being measured. A microchip is positioned within the housing and operatively communicates with the membrane for transmitting a digital signal indicative of the parameter. The microchip comprises an array of photoelectric cells for use with an LED for transmitting light at the photoelectric cells. A shutter is connected to the membrane and moveable between the photoelectric cells and the LED in response to deforming of the membrane.

17 Claims, 11 Drawing Sheets

U.S. PATENT DOCUMENTS

| | | | |
|---|---|---|---|
| 4,361,153 A | | 11/1982 | Slocum et al. |
| 4,407,296 A | | 10/1983 | Anderson |
| 4,485,813 A | | 12/1984 | Anderson et al. |
| 4,532,932 A | | 8/1985 | Batty, Jr. |
| 4,610,256 A | * | 9/1986 | Wallace ................. 600/488 |
| 4,621,628 A | | 11/1986 | Brudermann |
| 4,650,547 A | | 3/1987 | Gough |
| 4,796,643 A | | 1/1989 | Nakazawa et al. |
| 4,815,469 A | | 3/1989 | Cohen et al. |
| 4,846,191 A | | 7/1989 | Brockway et al. |
| 4,967,755 A | | 11/1990 | Pohndorf |
| 5,028,918 A | | 7/1991 | Giles et al. |
| 5,067,491 A | * | 11/1991 | Taylor, II et al. ........ 600/561 |
| 5,105,190 A | | 4/1992 | Kip et al. |
| 5,105,829 A | | 4/1992 | Fabian et al. |
| 5,127,913 A | | 7/1992 | Thomas, Jr. |
| 5,252,962 A | | 10/1993 | Urbas et al. |
| 5,279,309 A | | 1/1994 | Taylor et al. |
| 5,300,120 A | | 4/1994 | Knapp et al. |
| 5,322,063 A | | 6/1994 | Allen et al. |
| 5,325,873 A | | 7/1994 | Hirschi et al. |
| 5,330,520 A | | 7/1994 | Maddison et al. |
| 5,353,800 A | | 10/1994 | Pohndorf et al. |
| 5,398,691 A | | 3/1995 | Martin et al. |
| 5,404,877 A | | 4/1995 | Nolan et al. |
| 5,411,503 A | | 5/1995 | Hollstien et al. |
| 5,417,688 A | | 5/1995 | Elstrom et al. |
| 5,422,636 A | | 6/1995 | Urbas et al. |
| 5,435,310 A | | 7/1995 | Sheehan et al. |
| 5,481,262 A | | 1/1996 | Urbas et al. |
| 5,513,636 A | | 5/1996 | Palti |
| 5,540,691 A | | 7/1996 | Elstrom et al. |
| 5,551,427 A | | 9/1996 | Altman |
| 5,564,434 A | | 10/1996 | Halperin et al. |
| 5,566,676 A | | 10/1996 | Rosenfeldt et al. |
| 5,584,838 A | | 12/1996 | Rona et al. |
| 5,674,288 A | | 10/1997 | Knapp et al. |
| 5,702,421 A | | 12/1997 | Schneidt |
| 5,704,352 A | | 1/1998 | Tremblay et al. |
| 5,715,827 A | * | 2/1998 | Corl et al. ................. 600/486 |
| 5,716,407 A | | 2/1998 | Knapp et al. |
| 5,725,552 A | | 3/1998 | Kotula et al. |
| 5,725,578 A | | 3/1998 | Knapp et al. |
| 5,743,267 A | | 4/1998 | Nikolic et al. |
| 5,833,603 A | * | 11/1998 | Kovacs et al. ............. 600/317 |
| 5,855,609 A | | 1/1999 | Knapp |
| 5,879,366 A | | 3/1999 | Shaw et al. |
| 5,913,820 A | | 6/1999 | Bladen et al. |
| 5,957,966 A | | 9/1999 | Schroeppel et al. |
| 5,963,132 A | | 10/1999 | Yoakum |
| 5,977,431 A | | 11/1999 | Knapp et al. |
| 5,993,395 A | * | 11/1999 | Shulze ...................... 600/488 |
| 5,999,857 A | | 12/1999 | Weijand et al. |
| 6,021,352 A | | 2/2000 | Christopherson et al. |
| 6,024,704 A | * | 2/2000 | Meador et al. ............. 600/486 |
| 6,034,296 A | | 3/2000 | Elvin et al. |
| 6,053,873 A | | 4/2000 | Govari et al. |
| 6,053,918 A | | 4/2000 | Spievack |
| 6,074,394 A | | 6/2000 | Krause |
| 6,106,476 A | * | 8/2000 | Corl et al. ................. 600/486 |
| 6,113,553 A | | 9/2000 | Chubbuck |
| 6,115,636 A | | 9/2000 | Ryan |
| 6,117,086 A | * | 9/2000 | Shulze ...................... 600/488 |
| 6,140,740 A | | 10/2000 | Porat et al. |
| 6,159,156 A | | 12/2000 | Van Bockel |
| 6,162,228 A | | 12/2000 | Durham |
| 6,174,322 B1 | | 1/2001 | Schneidt |
| 6,181,973 B1 | | 1/2001 | Ceron et al. |
| 6,185,464 B1 | | 2/2001 | Bonner et al. |
| 6,214,029 B1 | | 4/2001 | Thill et al. |
| 6,216,029 B1 | | 4/2001 | Paltieli |
| 6,234,973 B1 | * | 5/2001 | Meador et al. ............. 600/486 |
| 6,237,398 B1 | | 5/2001 | Porat et al. |
| 6,239,724 B1 | | 5/2001 | Doron et al. |
| 6,240,322 B1 | | 5/2001 | Peterfeso et al. |
| 6,259,937 B1 | | 7/2001 | Schulman et al. |
| 6,261,247 B1 | | 7/2001 | Ishikawa et al. |
| 6,277,078 B1 | | 8/2001 | Porat et al. |
| 6,309,350 B1 | | 10/2001 | VanTassel et al. |
| 6,312,465 B1 | | 11/2001 | Griffin et al. |
| 6,328,699 B1 | | 12/2001 | Eigler et al. |
| 6,328,727 B1 | | 12/2001 | Frazier et al. |
| 6,370,418 B1 | | 4/2002 | Bernoski |
| 6,374,134 B1 | | 4/2002 | Bladen et al. |
| 6,385,484 B2 | | 5/2002 | Boksberger et al. |
| 6,405,091 B1 | | 6/2002 | Vachon et al. |
| 6,409,674 B1 | | 6/2002 | Brockway et al. |
| 6,411,842 B1 | | 6/2002 | Cigaina et al. |
| 6,442,413 B1 | | 8/2002 | Silver |
| 2002/0052604 A1 | | 5/2002 | Simon et al. |

FOREIGN PATENT DOCUMENTS

| | | |
|---|---|---|
| EP | 420177 A1 | 4/1991 |
| EP | 0 646 365 A1 | 4/1995 |
| EP | 0 897 690 A1 | 2/1999 |
| EP | 1 004 267 A2 | 5/2000 |
| EP | 1 050 265 A | 11/2000 |
| EP | 1 216 655 A | 6/2002 |
| JP | 60-70324 A | 4/1985 |
| WO | WO 83/03348 A1 | 10/1983 |
| WO | WO 93/02626 A1 | 2/1993 |
| WO | WO 94/04938 A1 | 3/1994 |
| WO | WO 96/05768 A1 | 2/1996 |
| WO | WO 97/13467 A1 | 4/1997 |
| WO | WO 97/33513 A1 | 9/1997 |
| WO | WO 99/17095 A1 | 4/1999 |
| WO | WO 99/33453 AL | 7/1999 |
| WO | WO 99/34453 AL | 7/1999 |
| WO | WO 99/34731 A1 | 7/1999 |
| WO | WO 99/48419 A1 | 9/1999 |
| WO | WO 00/16686 A2 | 3/2000 |
| WO | WO 00/32092 A1 | 6/2000 |
| WO | WO 00 74557 A1 | 12/2000 |
| WO | WO 01/36014 A2 | 5/2001 |
| WO | WO 02/38082 A1 | 5/2002 |

OTHER PUBLICATIONS

Steinhaus David M et al. "Initial Experience with an Implantable Hemodynamic Monitor", Circulation 1996;93No. 4:745–752.

Ohlsson A et al. "Continuous Ambulatory Haemodynamic Monitoring with an Implantable System", European Heart Journal 1998;19:174–184.

European Search Report EP 02253973 dated Mar. 21, 2003.

* cited by examiner

IMPLANTABLE TELEMETRIC MEDICAL SENSOR AND METHOD

FIELD OF THE INVENTION

The present invention relates, in general, to telemetric medical devices. More particularly, the present invention relates to a novel telemetric medical system which is capable of various medical applications including the measurement of a parameter within a patient's body, particularly an organ. One such application of the present invention is as an implantable telemetric endocardial pressure system, its associated novel components and their novel methods of use.

BACKGROUND OF THE INVENTION

In general, the use of implantable medical sensors in a patient is known. One example for an implantable sensor is disclosed in U.S. Pat. No. 4,815,469 (Cohen et al.) incorporated herein by reference. The disclosure is directed to an implantable medical sensor which determines the oxygen content of blood. The sensor includes a miniaturized hybrid circuit that includes light-emitting diode means, phototransistor means, and a substrate to which the light-emitting diode means and phototransistor means are bonded in a desired circuit configuration. The hybrid circuit is hermetically sealed within a cylindrical body made from a material that is substantially transparent to light, such as glass. Feedthrough terminals provide means for making an electrical connection with the hybrid circuit. The light-emitting diode means is driven with a stair-stepped current pulse. The purpose of the sensor is to sense the reflective properties of body fluid, such as blood, for spectrophotometric analysis. In one embodiment, the sensor is embedded within a bilumen pacemaker lead and positioned near the distal electrode of the lead so that the sensor resides within the heart when the lead is implanted within a patient, thereby allowing the sensed oxygen content of the blood within the heart to be a physiological parameter that can be used to control the pacing interval of a rate-responsive pacemaker.

U.S. Pat. No. 5,353,800 (Pahndorf et al.) discloses an implantable pressure sensor lead having a hollow needle adapted to be screwed into a patient's heart. The pressure sensor is supplied electrical power through conductors in the sensor.

There are cases where permanent positioning of the sensor is needed. One such case, for example, is disclosed in U.S. Pat. No. 5,404,877 (Nolan et al.), which is incorporated herein by reference. A leadless implantable cardiac arrhythmia alarm is disclosed which continuously assesses a patient's heart function to discriminate between normal and abnormal heart functioning and, upon detecting an abnormal condition, generates a patient-warning signal. The alarm is capable of sensing impedance measurements of heart, respiratory and patient motion and, from these measurements, generating an alarm signal when the measurements indicate the occurrence of a cardiac arrhythmia. It is important to note that the sensor uses an antenna system having a coil inductor for generating an electromagnetic field into tissue for detecting changes in impedance which relate to a physiological phenomena. For example, the size of the inductor is preselected in order to match the dimensions of the organ or structure to be measured.

There are also several known implantable devices that employ telemetry for transmitting or receiving data from an external device. One such device is, for example, the system disclosed in U.S. Pat. No. 6,021,352 (Christopherson et al.). The device utilizes a pressure sensor as a transducer for sensing respiratory effort of the patient. Respiratory waveform information is received by an implantable pulse generator (IPG)/simulator from a transducer and inspiration synchronous simulation is provided by the IPG.

One other telemetric implantable device is disclosed in U.S. Pat. No. 5,999,857 (Weijand et al.). This reference discloses a telemetry system for use with implantable devices such as cardiac pacemakers and the like, for two-way telemetry between the implanted device and an external programmer. The system employs oscillators with encoding circuits for synchronous transmission of data symbols in which the symbols form the telemetry carrier. The system provides circuits for higher density data encoding of sinusoidal symbols, including combinations of BPSK, FSK, and ASK encoding. Embodiments of transmitters for both the implanted device and the external programmer, as well as modulator and demodulator circuits, are also disclosed. It is important to note that the implant device has its own power supply in the form of a battery for powering all of the circuitry and components of the implanted device.

It is also important to note, that to date, there has not been any telemetric medical system that is both a highly efficient system due to its components and their ease of use while providing extremely accurate information regarding a measured parameter in a patient's body.

SUMMARY OF THE INVENTION

The present invention is directed to a novel telemetric medical system for use with various medical applications such as monitoring medical conditions or measuring parameters within a patient's body for different types of organs, including tissue, as well as their function.

The present invention is a telemetric medical system comprising a telemetric medical sensor for implantation in a patient's body for measuring a parameter therein. The sensor comprises a housing, and a membrane at one end of the housing, wherein the membrane is deformable in response to the parameter. A microprocessor, which is in the form of a microchip, is positioned within the housing and operatively communicates with the membrane for transmitting a signal indicative of the parameter.

A signal reading and charging device is locatable outside of a patient's body and communicates with the sensor. The signal reading and charging device comprises a casing and a circuit within the casing. The circuit comprises a logic control unit and a processing unit operatively connected to the logic control unit. The logic control unit, through a deep detector, receives the transmitted signal from the sensor. The logic control unit also sends a powering signal to the sensor through a sine wave driver for remotely powering the sensor. The powering signal is a sinusoidal wave signal approximately 4–6 MHz. The processing unit includes an algorithm for converting the transmitted signal received from the sensor into a measured parameter. Additionally, the signal reading and charging device includes a power source operatively connected to the circuit and a power switch for activating and deactivating the device.

The signal reading and charging device also includes an antenna coil for sending the powering signal to the sensor and for receiving the transmitted digital signal from the sensor. The antenna coil has inductive coupling with the sensor. The signal reading and charging device also includes a display, which is an LCD screen, for displaying the measured parameter.

The microprocessor, which is in the form of a microchip, comprises an array of photoelectric cells which are arranged in staggered rows. The array also includes a reference photoelectric cell located at one end of the array. A light emitting diode (LED) transmits light at the photoelectric cells and the reference photoelectric cell.

The sensor further comprises a shutter connected to the membrane and moveable between the photoelectric cells and the LED in response to the deforming of the membrane. The sensor is arranged such that the reference photoelectric cell is not blocked by the shutter and remains exposed to the light emitted by the LED.

The microchip further comprises a plurality of comparators operatively connected to the photoelectric cells and a buffer operatively connected to the comparators for storing and transmitting the digital signal. The sensor further comprises an antenna, in the form of a coil, operatively connected to the microchip wherein the antenna is located at the exterior of the housing. Alternatively, the antenna is located within the housing of the sensor. Preferably, the antenna coil is made of wire comprising silver and platinum iridium. Additionally, the antenna has 20–25 turns.

The sensor according to the present invention further comprises a plurality of anchoring legs resiliently attached to the housing for anchoring the sensor into tissue. Additionally, the housing optionally includes a notch in an outer surface of the housing to facilitate deployment. The housing further optionally includes a circumferential groove at the notch to further facilitate deployment.

In another embodiment for the sensor, the housing further includes a tapered end and a piercing tip thereon. The tapered end further includes helical threads thereon for threading the sensor housing directly into tissue. An alternative embodiment includes a plurality of tissue barbs on the tapered end for anchoring the sensor housing directly into tissue.

The present invention also includes a method for telemetrically measuring a parameter in a patient's body comprising the steps of providing a telemetric medical sensor comprising a housing having a membrane at one end of the housing wherein the membrane is deformable in response to the parameter, and a microchip is positioned within the housing and operatively communicates with the membrane for transmitting a signal indicative of the parameter. The sensor is implanted at a site within the patient's body and the parameter is telemetrically measured from outside of the patient's body with a signal reading and charging device. The method also includes telemetrically powering the sensor from outside of the patient's body with the signal reading and charging device. The measured parameter is then displayed on the display of the signal reading and charging device.

The method according to the present invention also includes a method for telemetrically measuring a parameter in a patient's heart wherein the method comprises the steps of imaging the heart, through the use of transesophageal ultrasonic imaging, and identifying an implantation site in the heart. An opening is created in the tissue at the implantation site and a sensor comprising a housing, a membrane at one end of the housing wherein the membrane is deformable in response to the parameter, and a microchip positioned within the housing and operatively communicating with the membrane for transmitting a signal indicative of the parameter is provided. The sensor is placed within the opening and the parameter is telemetrically measured from outside of the patient's body based on the transmitted signal by the sensor.

The method also includes telemetrically powering the sensor from outside of the patient's body and displaying the measured parameter with a signal reading and charging device. Parameter measurements are made multiple times per second with the signal reading and charging device.

According to the present invention, the sensor is positioned within a chamber of the heart by using the septum as an implantation site, for instance, the fossa ovalis. Alternatively, the sensor is positionable at other anatomical sites within the heart and other organs and tissue.

One parameter that is measured with the system and method according to the present invention is hemodynamic blood pressure in a chamber of the heart.

Accordingly, the method according to the present invention further includes taking between 10–20 parameter measurements per second.

Moreover, the method further includes creating the opening in the tissue with a needle. In one embodiment of the present invention, the sensor includes a plurality of anchoring legs on the sensor for anchoring the sensor to the tissue. Additionally, the sensor is coated with a nonthrombogenic agent in order to prevent thrombosis within the heart upon implantation of the sensor.

Another embodiment of the method according to the present invention includes a method for telemetrically measuring a parameter in a patient's heart wherein the method comprises the steps of imaging the heart with transesohageal ultrasonic imaging and identifying an implantation site in the heart. A sensor comprising a housing and a membrane at one end of the housing wherein the membrane is deformable in response to the parameter and a tapered distal end and piercing tip at the other end of the housing is provided. The sensor further comprises a microchip positioned within the housing and operatively communicating with the membrane for transmitting a signal indicative of the parameter. The sensor is implanted at the site with the piercing tip and the tapered distal end of the sensor. The parameter is telemetrically measured from outside of the patient's body based on the transmission signal by the sensor. Additionally, the sensor is telemetrically powered from outside of the patient's body. A signal reading and charging device is used outside of the patient's body to measure the parameter, power the sensor, and display the measured parameter. Accordingly, parameter measurements are made multiple times per second with the signal reading and charging device.

The sensor is positioned within a chamber of the heart and the implantation site is the septum, for instance, at the fossa ovalis. With the system and method according to the present invention, one parameter that is measured is hemodynamic blood pressure within a chamber of the heart. For instance, 10–20 parameter measurements are made per second for monitoring blood pressure in accordance with the present invention.

Alternatively, the sensor includes helical threads on the tapered distal end of the sensor and the sensor is anchored into the tissue at the site by threading the tapered distal end of sensor directly into the tissue. Alternatively, the sensor includes a plurality of tissue barbs on the tapered distal end of the sensor and the sensor is anchored into the tissue at the site with the tissue barbs.

The present invention will be more fully understood from the following detailed description of the preferred embodiments thereof, taken together with the drawings, in which:

DESCRIPTION OF THE PREFERRED EMBODIMENTS

Figure 8:
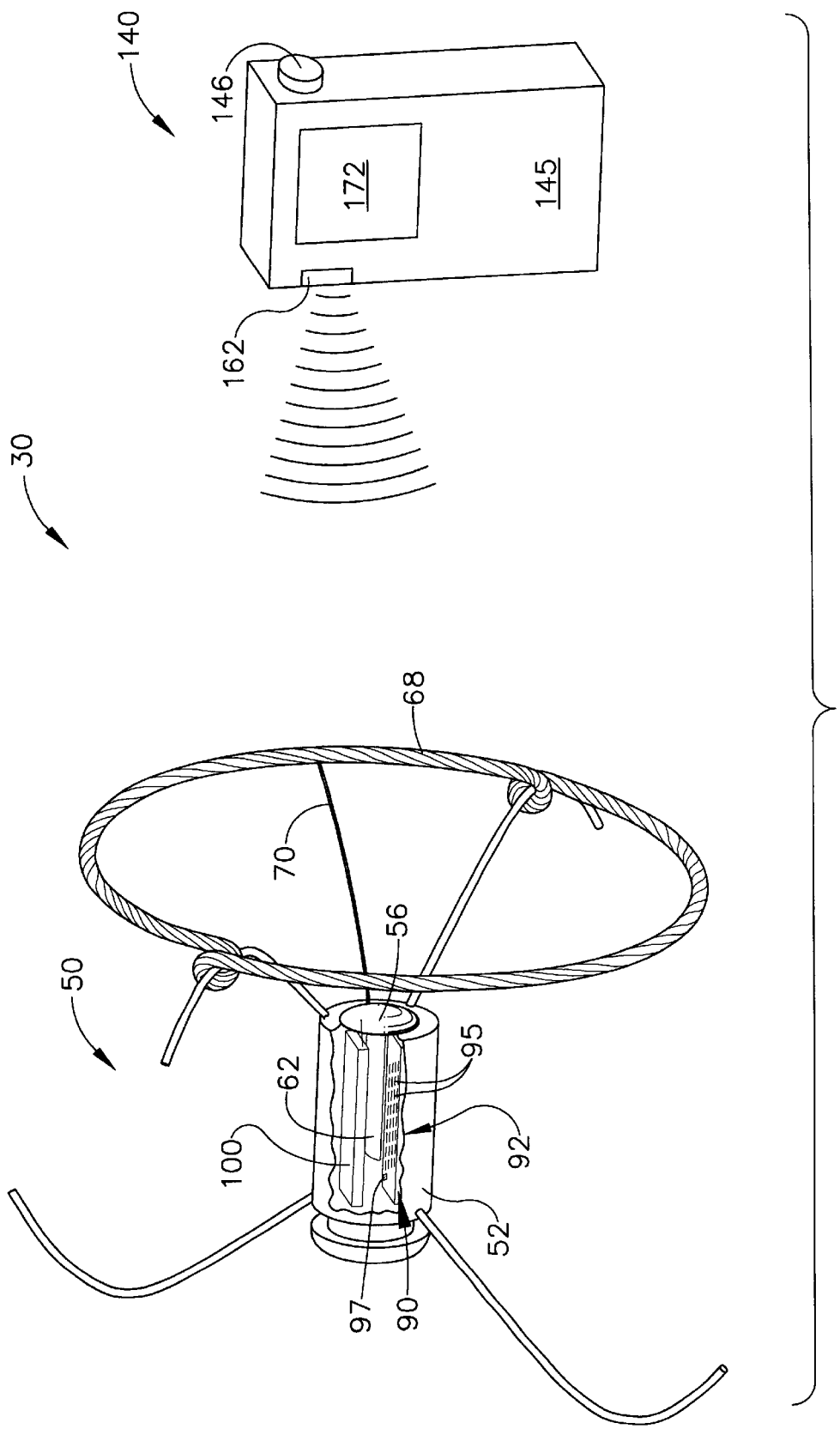
FIG. 8 is a schematic illustration depicting the telemetric system according to the present invention including the sensor of FIG. 1 and a signal reading and charging device remotely located from and in communication with the sensor.

The present invention relates to a novel telemetric medical system 30, as schematically illustrated in FIG. 8, as well as its novel components and methods of use useful for various medical applications, as explained and demonstrated herein.

One aspect of the system 30 of the present invention is to remotely sense and measure a characteristic or parameter (or number of various parameters including the magnitude of any parameter) within a patient's body, or within an organ or tissue of the patient's body, through the use of a novel implantable telemetric medical sensor 50, which is completely wireless, and a novel signal reading and charging device 140 which operatively communicates with the sensor 50.

Telemetric Sensor

Figure 1:
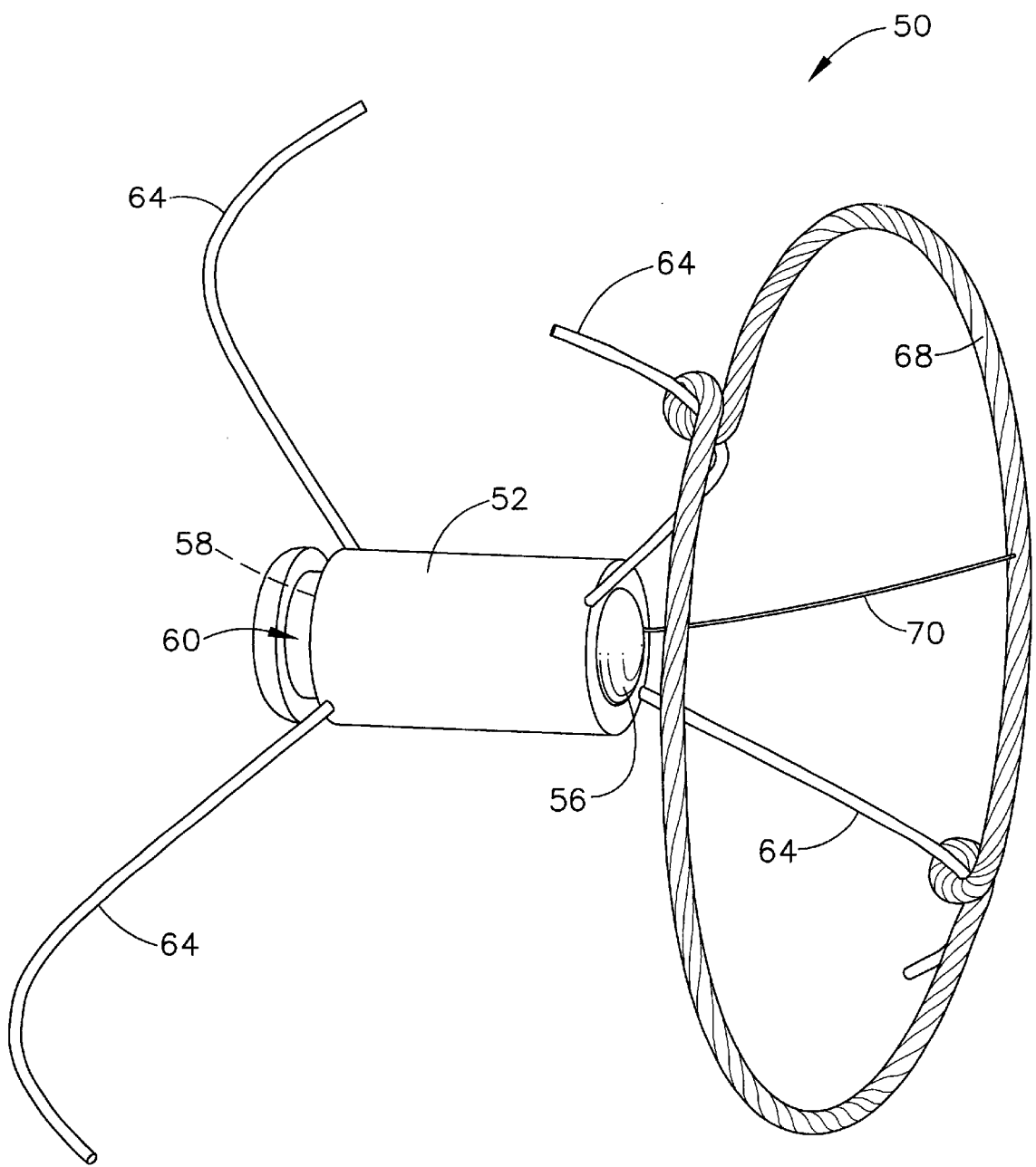
FIG. 1 is a schematic illustration of a telemetric implantable medical sensor according to the present invention.

As schematically illustrated in FIG. 1, the sensor 50 comprises a housing 52 made of a biocompatible material such as polysilicon or titanium. The housing 52 preferably has a cylindrical shape although any type of shape for the housing 52 is acceptable. The housing 52 has an approximate length ranging between 4–5 mm and an approximate diameter ranging from 2.5–3 mm in diameter. The housing 52 can also be smaller, e.g. 3 mm in length and a 1–2 mm outer diameter. The housing 52 includes cylindrical walls that are approximately 250 µm in thickness. A flexible membrane 56 made of a deformable material is fixed to one end of the housing 52. A notch 58 and a circumferential groove 60 are provided on an exterior surface of the housing 52 for facilitating delivery and implantation of the sensor 50.

The membrane 56 is made of a flexible or deformable material such as polysilicon rubber or polyurethane. The membrane 56 has an approximate thickness of 20 µm and has a diameter ranging from approximately 1.5–2 mm. The membrane 56 is normally biased outwardly from the housing 52 due to the interior pressure within the housing 52. The membrane 56 is forced to bulge inwardly into the housing 52 whenever the pressure exterior of the housing 52 exceeds the internal pressure within the housing 52.

Since the membrane 56 is deformable and normally biased outwardly from the housing 52, the membrane 56 responds directly to the environment of the tissue or organ being monitored and/or measured for a particular characteristic or parameter. In response to even the slightest changes in these characteristics or parameters, the membrane 56 deforms inwardly toward the interior of the housing 52. Accordingly, there is a direct relationship or correspondence between any change in measured characteristic or parameter and the amount or degree of deforming action or movement of the membrane 56.

It is important to note that the membrane 56 has a relatively large area in dimension when compared to solid state membrane devices, such as piezoelectric sensors or fabricated memory chips utilizing membranes. Accordingly, the requirements from the electronics of the sensor 50 are less demanding. Additionally, the membrane 56 has a much larger deflection than that of the solid state membrane.

Figure 2:
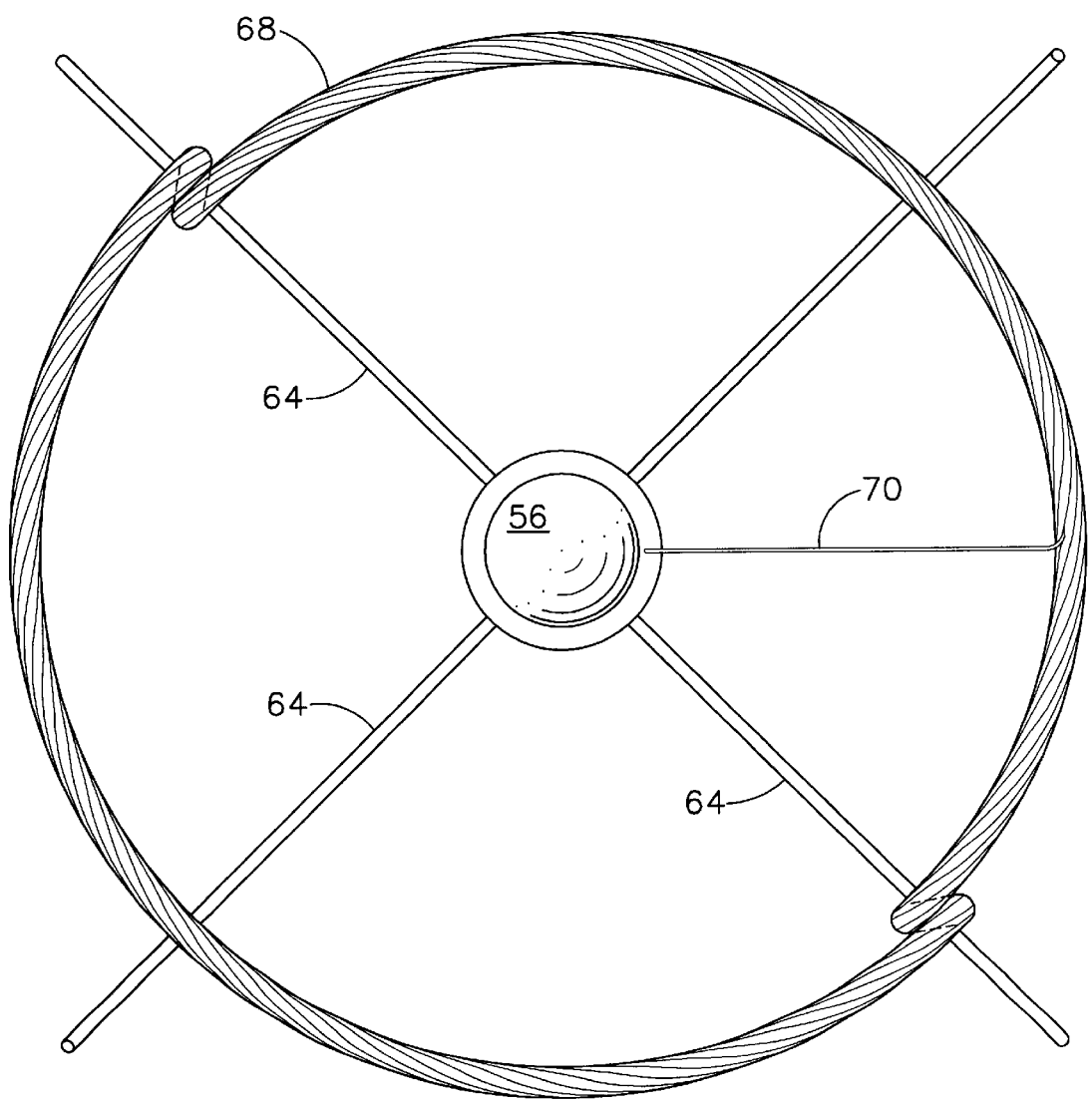
FIG. 2 is a top view of the sensor of FIG. 1.

The sensor 50 also includes an antenna coil 68 which is operatively connected to the internal components of the sensor 50 by an antenna lead 70. The antenna coil 68 is an inductance coil having a spiralled coil configuration. The material used for the antenna wire is approximately 90% silver content with a cladding of platinum iridium of approximately 10% content. The antenna coil 68 is preferably made of 20–25 turns of 30 µm thickness wire. The antenna outer diameter is 1.5–2.0 cm (FIG. 2).

Accordingly, due to these features, the antenna coil 68 possesses a very low parasitic capacitance. Additionally, the antenna coil 68, due to its silver/platinum content wire has extremely high conductivity and is extremely flexible.

Although antenna 68 is described as being external of the housing 52, it is well within the scope of the invention to include any type of suitable antenna, such as an antenna that is contained within the housing 52.

The sensor 50 further includes anchoring legs 64 resiliently biased to the exterior of the housing 52. The number of anchoring legs 64 can vary depending on the desired degree of anchoring and geography of the anatomy in which the sensor 50 is to be placed. The anchoring legs 64 are made from wire utilizing shape memory metal material, such as a nickel titanium alloy (NiTinol). The anchoring legs 64 have a concave configuration with a radius of curvature that curves into the tissue or organ in which the sensor 50 is to be anchored. Other appropriate configurations for the anchoring legs 64 are also contemplated herein.

If desireable, the sensor 50 is coated with a nonthrombogenic or anticoagulating agent such as Heparin prior to implantation in order to prevent thrombosis, clotting, etc.

Figure 3:
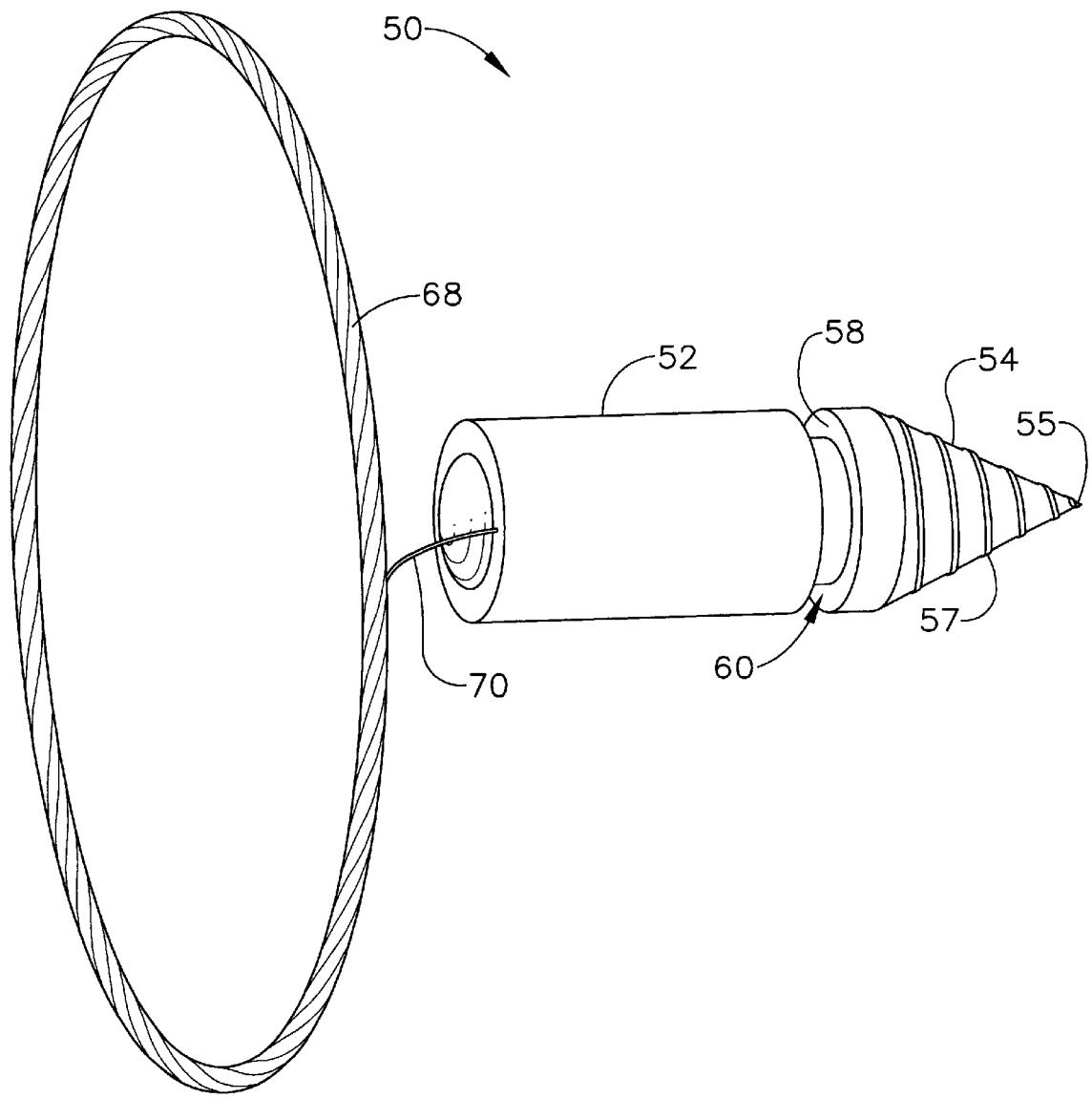
FIG. 3 is a schematic illustration of an alternative embodiment of the sensor of FIG. 1 having a tapered distal end with helical threads and tissue piercing tip for anchoring into tissue.

FIG. 3 illustrates an alternative embodiment of the sensor 50 having a tapered end 54 on the housing 52. The tapered end 54 has a tissue piercing tip 55 and helical threads 57 arranged on an outer surface of the tapered end 54 in order to facilitate the direct anchoring of the tapered end 54 of the housing 52 through direct threading into tissue.

Figure 4:
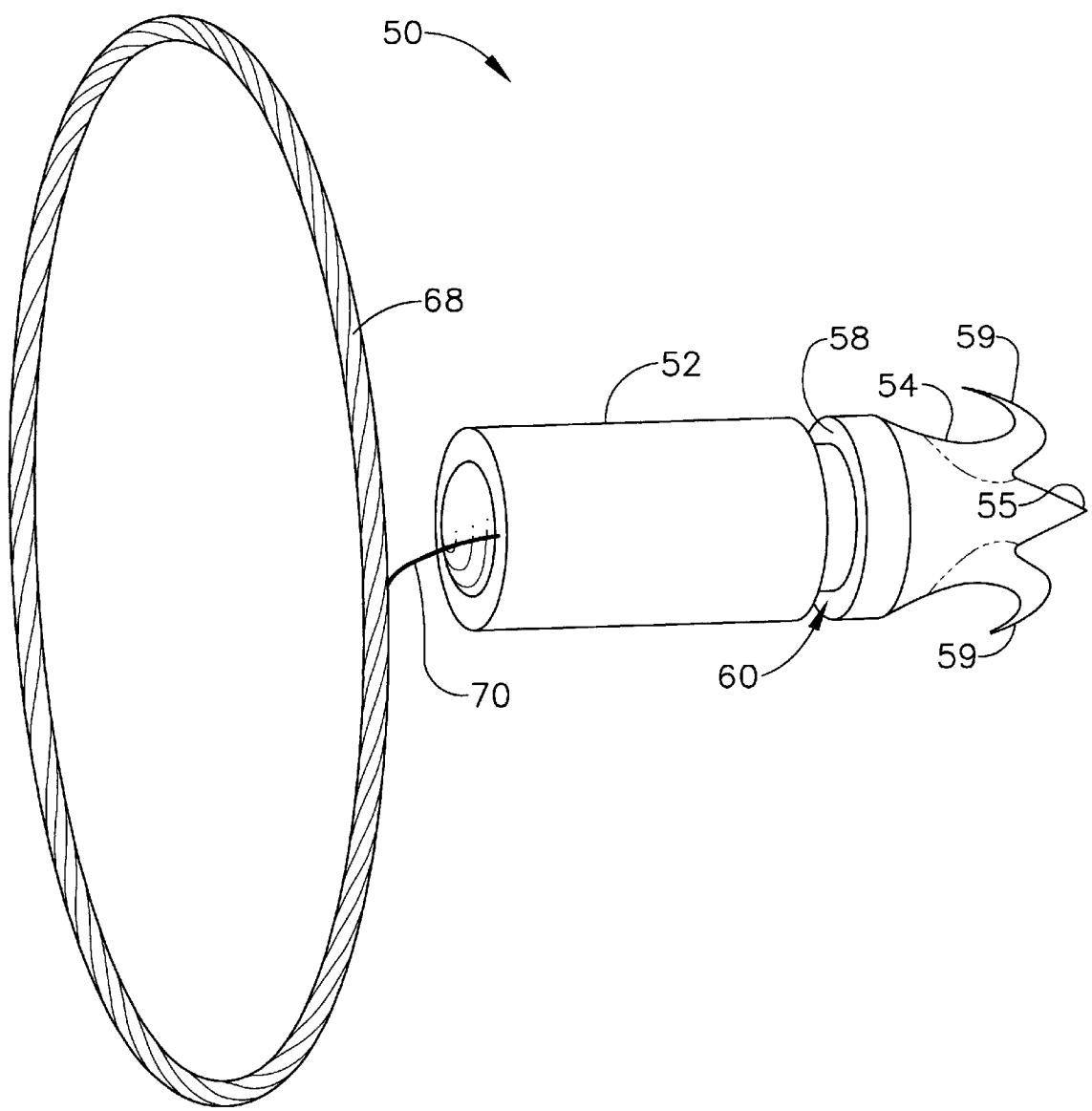
FIG. 4 is another alternative embodiment of the sensor of FIG. 1 having a tapered distal end with tissue piercing tip and a plurality of tissue piercing barbs thereon.

FIG. 4 illustrates another alternative embodiment sensor 50 including a plurality tissue barbs 59 fixed to the tapered end 54 of the housing 52. The barbs 59 have a tissue piercing tip curved outwardly away from the tissue piercing tip 55. Accordingly, along with the tissue piercing tip 55, the tissue barbs 59 grasp firmly into the tissue for firmly anchoring the housing 52 in the tissue.

Figure 5:
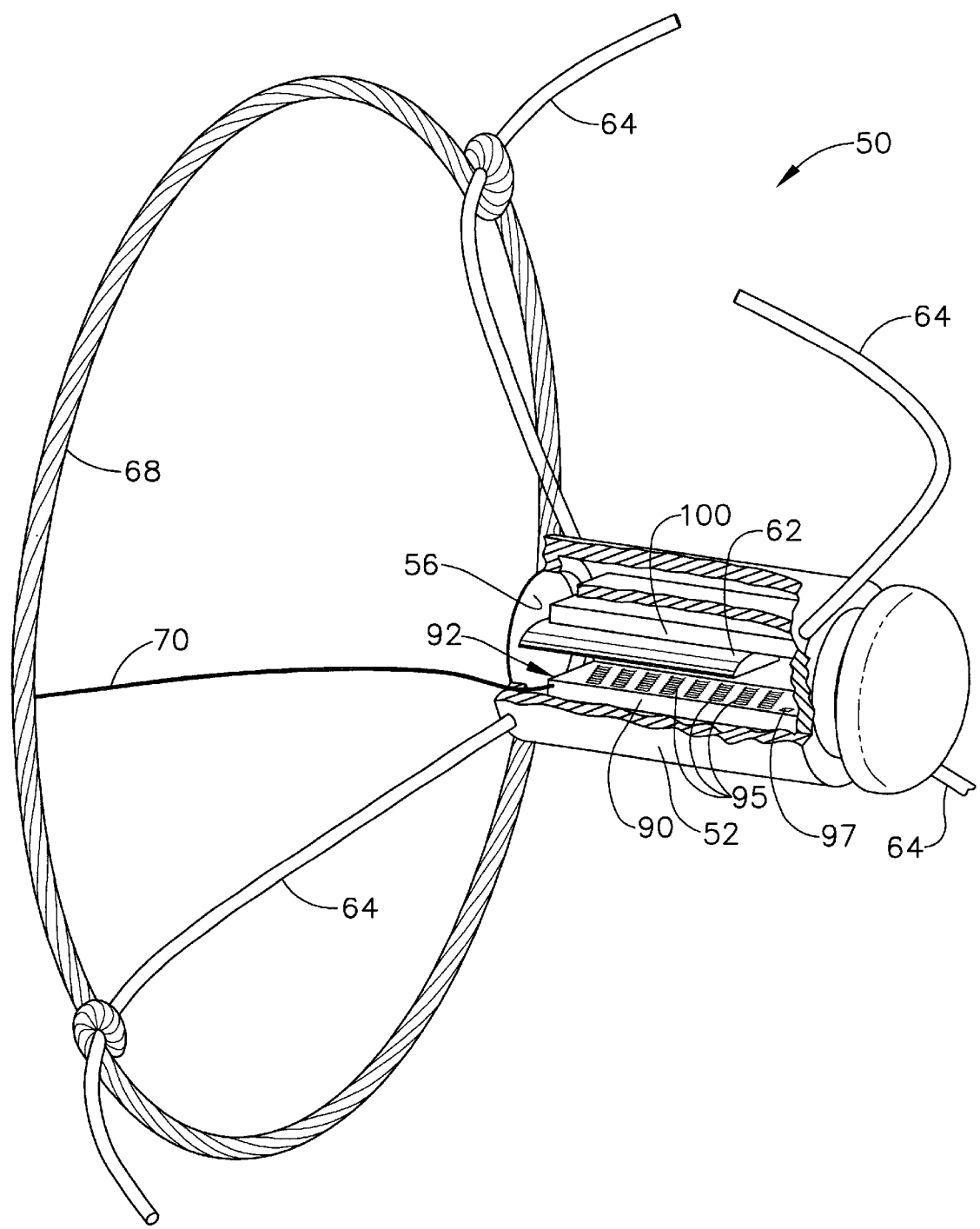
FIG. 5 is a partial perspective view of the sensor of FIG. 1 with some parts removed in order to reveal the internal components of the sensor.
Figure 7:
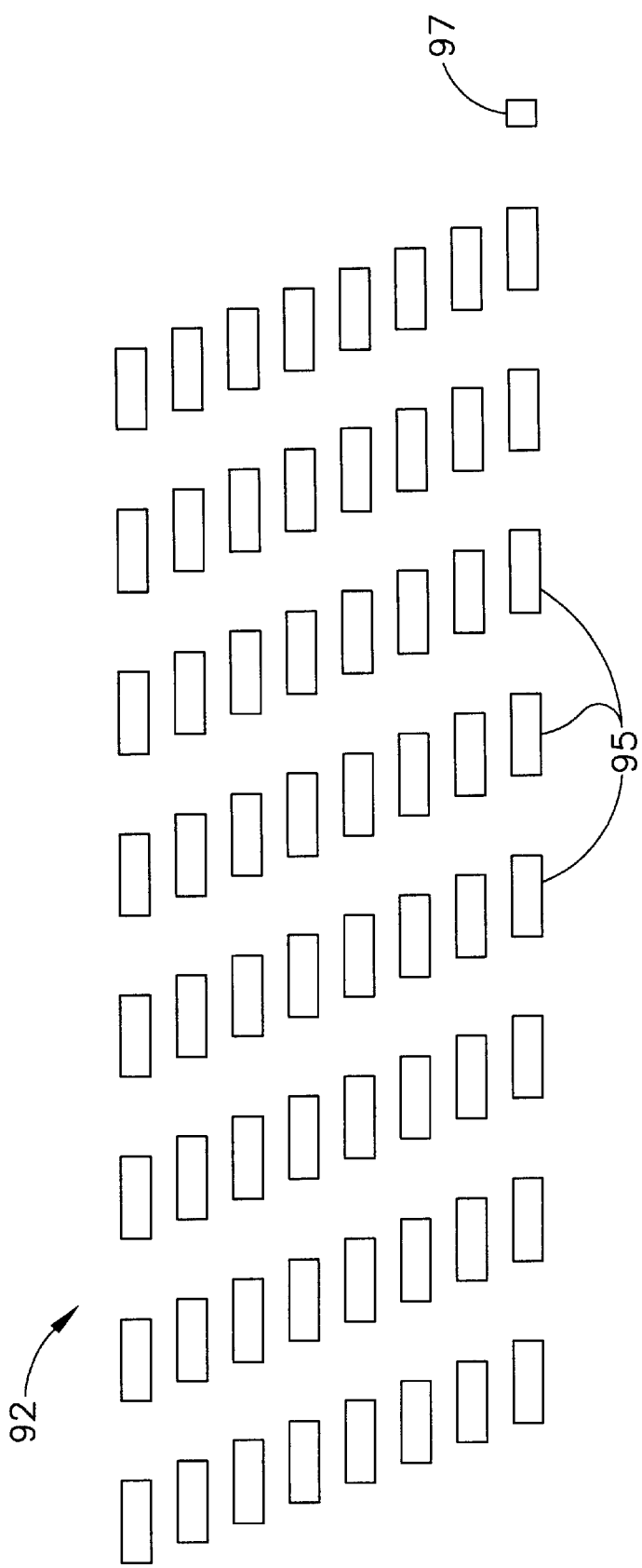
FIG. 7 is a schematic illustration depicting an array of photoelectric cells for the sensor according to the present invention.

As shown in FIG. 5, the interior of the housing 52 includes a microprocesser 90, in the form of a microchip, fixed within one of the interior walls of the housing 52. The lead 70 of the antenna coil 68 is operatively connected to the microprocessor 90. Microprocessor 90 includes an array 92 of photoelectric cells 95 arranged in a patterned confirguration, e.g. eight staggered rows containing eight photoelectric cells 95 in each row. A reference photoelectric cell 97 is located at one end of the array 92 resulting in an array 92 having a total of sixty-five photoelectric cells such as illustrated in FIG. 7. The photoelectric cell array 92 provides for 64 degrees of resolution. The pitch distance between each photocell 95 is approximately ¼ the size of a photocell 95. Additionally, the reference photocell 97 has a dimension that is approximately the size of the pitch, e.g. ¼ the size of a photocell 95, thus providing a resolution that is equal to a motion of ¼ of the photocell.

A light emitting diode (LED) 100 is operatively connected to the microprocessor 90 and is positioned above and spaced parallel and away from the photoelectric cell array 92. A shutter 62 is connected to the inner surface of the membrane 56 and extends logitudinally from the membrane 56 within housing 52. The shutter 62 has a substantially D-shaped configuration and logitudinally extends between the LED 100 and the photoelectric cell array 92. The shutter 62 is made from an aluminum alloy and is positioned such that the planar surface of the shutter 62 directly faces the photoelectric cell array 92. The shutter 62 is fixed to the deformable membrane 56 such that the shutter 62 moves in association with the membrane 56. Accordingly, when the membrane 56 is deflected inwardly into the housing 52 (due to the monitored or measured tissue or organ parameter), the shutter 62 logitudinally extends over a number of photoelectric cells 95 in the array 92 in direct relation to the inward movement of the membrane 56 as it is being deformed. Likewise, when the membrane 56 is deflected outwardly from the housing 52, the shutter 62 moves logitudinally outwardly from the end of the housing 52 along with the membrane 56. Accordingly, the shutter 62 obscures or blocks a number of the photoelectric cells 95 in accordance with the degree of movement of the membrane 56. Thus, when the shutter 62 is positioned over a specific number of photoelectric cells 95, light from the LED 100 is prevented from reaching the photoelectric cells 95 and affects signal transmission from these cells 95. This arrangement constitutes an analog-to-digital (A/D) conversion which is power effective since there is a simple counting of the number of photocells that are on or off as a measure of the shutter's motion. Hence, the analog-to-digital conversion. Accordingly, the microprocessor 90 operatively communicates with the membrane 56.

The reference photoelectric cell 97 is never obscured or covered by the shutter 62 since it is located at the far end (end away from the membrane 56) of the array 92. The shutter 62 and membrane 56 are calibrated such that even upon maximum deflection inwardly into the housing 52, it results in the reference photoelectric cell 97 being permanently exposed to the LED 100 for use as a reference signal for the sensor 50. Yet, the power dissipation of the photocell is very low.

Figure 6A:
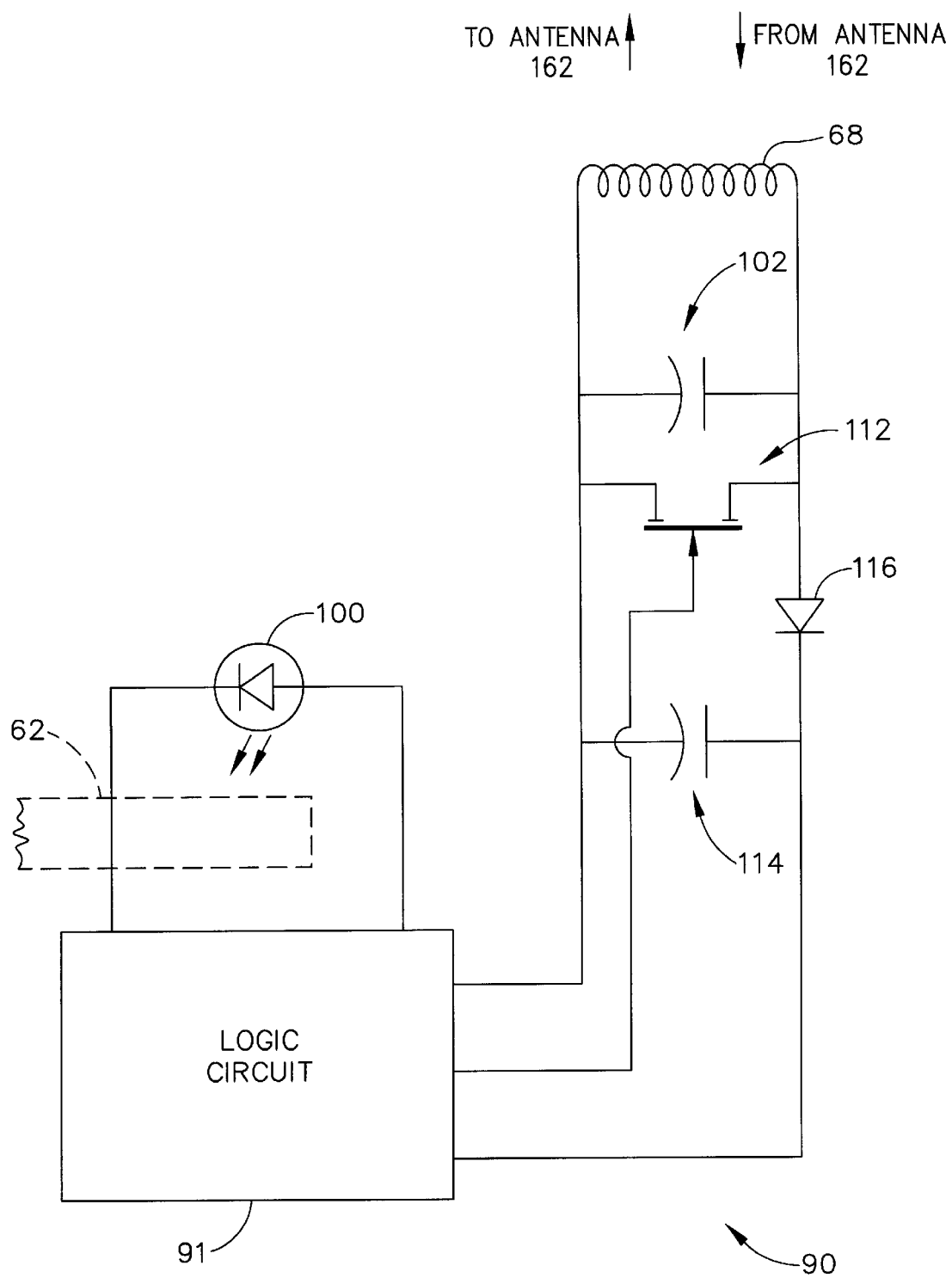
FIG. 6A is schematic diagram illustrating a microprocessor circuit for the sensor according to the present invention.
Figure 9:
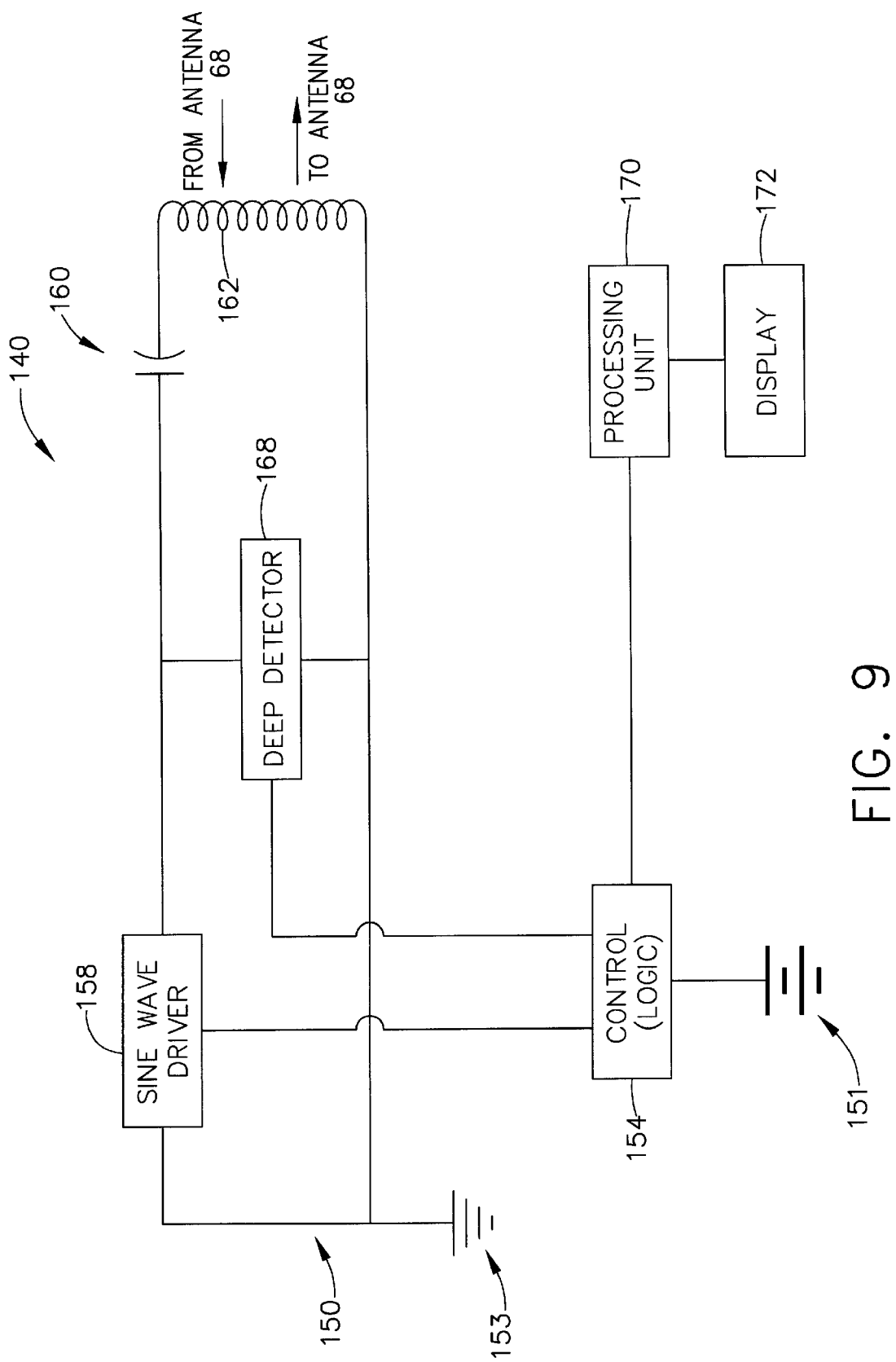
FIG. 9 is a schematic diagram illustrating a read/charge circuit for the signal reading and charging device of FIG. 8.

As best shown in FIG. 6A, the microprocessor 90 is a circuit wherein the antenna coil 68 and a resonance capacitor 102 operate as a resonating oscillator for the sensor 50. The antenna coil 68 receives transmitted RF signals sent by the signal reading and charging device 140 as illustrated in FIGS. 8 and 9. The RF signal received at the antenna coil 68 is a charging signal for powering the microprocessor 90. Upon receiving the RF charging signal, the antenna coil 68 and capacitor 102 resonate and charge a charge capacitor 114 through diode 116. Upon reaching a predetermined voltage threshold of approximately 1.2 V, the capacitor 114 powers the LED 100 and a logic circuit 91 through control unit 104. Upon powering of the LED 100 by the charged capacitor 114, the LED emits light to the photoelectric cell array 92 which is kept at negative voltage.

Figure 6B:
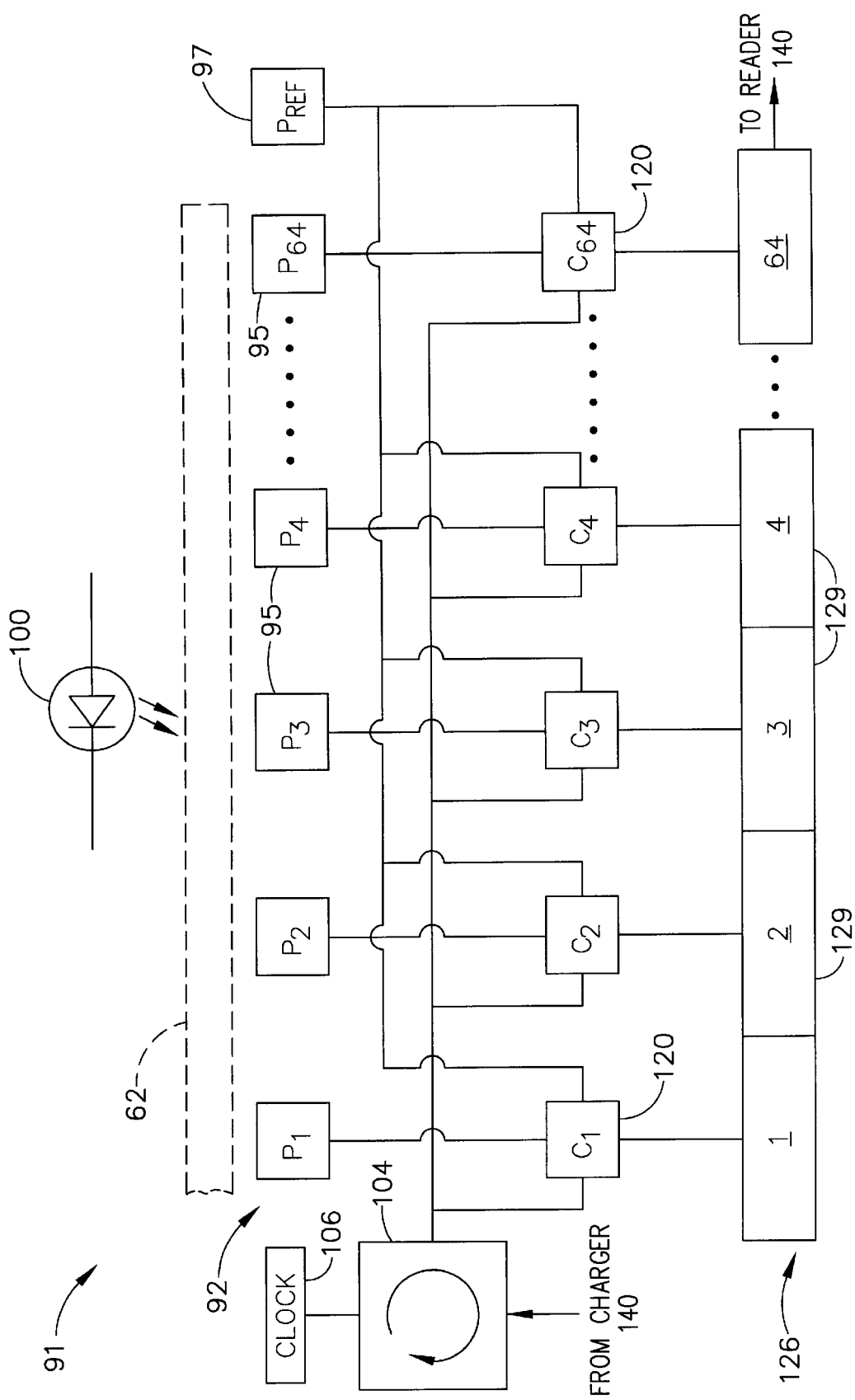
FIG. 6B is a schematic diagram illustrating a logic circuit for the microprocessor circuit of FIG. 6A.

As illustrated in FIG. 6B, the photoelectric cell array 92 is designated $P_1, P_2, \ldots P_{64}$ and $P_{ref}$, respectively. Each photoelectric cell 95 ($P_1$–$P_{64}$) are connected in parallel to a plurality of comparators 120 designated C1, C2 ... C64. The reference photoelectric cell 97 is operatively connected to each comparator 120 (C1–C64) for providing a reference signal to each comparator 120 in comparison to the signal received from each respective photoelectric cell 95. The logic circuit 91 is powered and controlled by the control unit 104 and a clock 106. The control unit 104 is connected to each comparator 120.

A buffer 126 having a plurality of buffer cells 129 (sixty-four total buffer cells corresponding to each comparator C1–C64) is operatively connected to the comparators 120. Each buffer cell 129 is a flip-flop, or memory cell, which receives a signal from its respective comparator C1–C64 resulting in a binary number which is sixty-four digits long (a series of ones or zeros). All buffer cells 129 are filled in a single clock cycle and each buffer 129 has either "0" or "1" in it. After all sixty-four buffer cells 129 have been filled with its respective binary number, the digital signal representing all sixty-four bytes is sent to the signal reading and charging device 140 by the control unit 104. After transmitting the digital signal, the control unit 104 is reset by the clock 106 awaiting further signal inputs from the signal reading and charging device 140. Encryption of the binary number is provided by the signal reading and charging device 140 described in greater detail below.

Upon filling the sixty-fourth buffer cell, the digital signal is transmitted from the buffer 126 and activates switch 112 resulting in a transmission of the digital signal from the antenna coil 68 to the antenna coil 162 of the signal reading and charging device 140.

One main aspect of the system 30 of the present invention is that the sensor 50 is both a wireless transponder and a low-powered device capable of fast update rate, despite its passive nature, due to the inherent analog-to-digital (A/D) conversion mechanism employed in the sensor 50, e.g. the photoelectric cell array 92, which directly converts the membrane 56 deflection into a digital signal, with no power consumption as would be required for a conventional electronic A/D converter.

Signal Reading and Charging Device

As illustrated in FIG. 8, the signal reading and charging device 140 according to the present invention is for use outside of a patient's body or at the exterior surface of the patient's body. The signal reading and charging device 140 includes a casing 145, which is a housing, having a liquid crystal display (LCD) display screen 172 mounted in an opening in the housing 145. The signal reading and charging device, also commonly referred to as a read/charge device, reader/charger or reader/charger device, is activated by a power switch or toggle 146 extending from the casing 145. Antenna coil 162 operatively communicates with the antenna coil 68 of the sensor 50 by inductance coupling.

As shown in FIG. 9, once the logic circuit 91 transmits the digital signal from the sensor 50 through sensor antenna coil 68, the coupling constant of the reader/charger antenna coil 162 is changed and is detected by a deep detector 168 operatively connected to the reader/charger antenna coil 162. The deep detector 168 is sensitized to detect a change in the amplitude of the signal for as low as a 0.01% change in amplitude.

A read/charge logic control unit 154 is operatively connected to the deep detector 168 for determining the threshold for the deep detector 168. The logic control unit 154 also includes a power source 151 for powering the components of the reader/charger device 140.

The reader/charger circuit 150 further includes a processing unit 170 operatively connected to the logic control unit 154. The processing unit 170 contains the algorithm for converting the digital signal received from the sensor 50 (FIG. 8) into a measured parameter for the medical parameter, condition or characteristic sensed at the implanted sensor 50. Additionally, the processing unit 170 includes encryption code for encryption of the digital signal (sixty-four bit signal) using encryption algorithms such as exclusive-OR (XOR), RSA methods (RSA Security, Inc.), etc.

For example, where the parameter being measured is hemodynamic blood pressure, within an organ such as the chamber of a heart, once the processing unit 170 receives the digital signal, the processing unit 170, through its algorithm, converts the digital signal (binary number) to a pressure value, using a look-up comparison table, or analytical expression representing the relation between the shutter 62 deflection in the sensor 50 versus the exterior sensor pressure at the membrane 56, which is given below:

$$P = (KD^3/A^2)X^2$$

where P is the pressure value, D is the thickness of the membrane, A is the membrane radius, X is the deflection from the equilibrium and K is a constant.

The LCD display 172 is operatively connected to the processing unit 170 for displaying the measured parameter (hemodynamic blood pressure in the example above) converted from the digital signal in real time.

By utilizing the signal reading and charging device 140 at the exterior of the patient's body, continuous parameter readings (for determining aspects of the parameter such as magnitude) are obtainable for both the mean and active or individual values of the sampled parameter.

When measuring characteristics of a body fluid such as blood, the signal reading and charging device 140 maintains an active reading volume around the sensor 50, ranging anywhere from 5–25 cm, and preferably, an active reading volume ranging approximately 10–15 cm. Moreover, with the telemetric medical system 30, through the sensor 50, and the signal reading and charging device 140, it is possible to sample multiple readings per second. Preferably, approximately 10–20 readings per second are possible with the present invention.

Other attributes associated with the present invention when utilized as a pressure monitor in a chamber of the heart include monitoring a pressure range of +/−30 mmHg; an accuracy (at 5 mSec. integration) of +/−1 mmHg with a repeatability (at 5 mSec. integration) of +/−1 mmHg. It is important to note that the pressure boundaries can be changed easily by changing the size and dimensions, such as width, of the membrane without any change to the electronics. This is important for allowing the present invention to be adapted for various applications while using the same design.

The control unit 154 is also operatively connected to a sine-wave driver 158 for generating a sinusoidal wave signal of approximately 4 to 6 MHz. The sinusoidal wave signal is generated by the sine-wave driver 158 through capacitor 160 to the reader/charger antenna coil 162 for transmission or sending to the antenna coil 68 of the sensor 50 in order to power or charge the sensor 50 as described above.

Medical Procedures

As mentioned above, the telemetric medical system 30 according to the present invention is useful for nearly any type of medical diagnostic procedure where it is desireable to implant the sensor 50 at a portion of the body, particularly tissue or organ of interest. The telemetric medical system 30 according to the present invention allows for remote monitoring and diagnosis of a condition of the tissue or organ by being able to rapidly sample various parameters or variables of any physical condition within the patient's body at the site of interest. Since the telemetric medical system 30 is wireless, these types of procedures are conducted in a completely non-invasive manner with minimal trauma to the patient.

Figure 10:
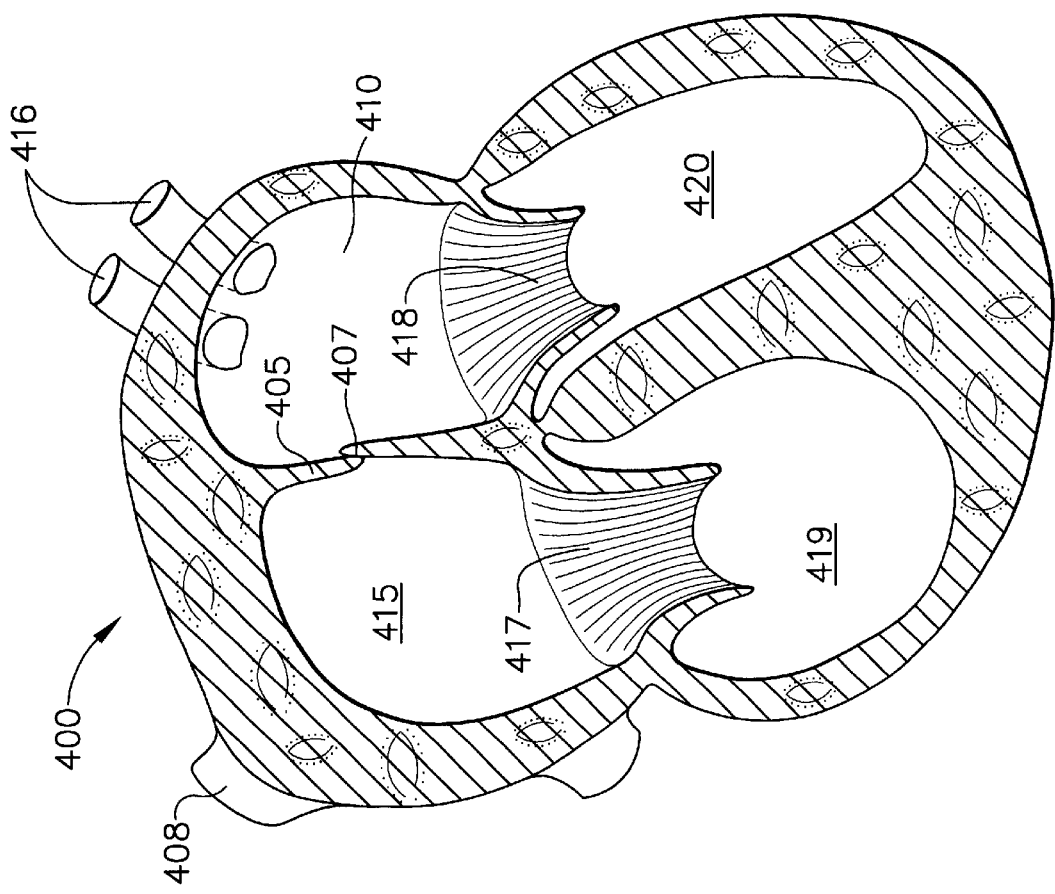
FIG. 10 is a schematic illustration of a patient's heart.

One particular example for the telemetric medical system 30 according to the present invention, its components and their method of use, is in the field of congestive heart failure (CHF). CHF is defined as a condition in which a heart 400 (FIG. 10) fails to pump enough blood to the body's other organs. This can result from narrowed arteries that supply blood to the heart muscle (due to coronary artery disease), past heart attack, or myocardial infarction, with scar tissue that interferes with the heart muscle's normal work, high blood pressure, heart valve disease due to past rheumatic fever (in valves such as semilunar valve, tricuspid valve 417 or mitral valve 418) or other causes, primary disease of the heart muscle itself, called cardiomyopathy, defects in the heart present at birth such as congenital heart disease, infection of the heart valves and/or heart muscle itself (endocarditis and/or myocarditis).

The ailing heart 400 keeps functioning but not as efficiently as it should. People with CHF cannot exert themselves because they become short of breath and tired. As blood flowing out of the heart 400 slows, blood returning to the heart 400 through the veins backs up, causing congestion in the tissues. Often swelling (edema) results, most commonly in the legs and ankles, but possibly in other parts of the body as well. Sometimes fluid collects in the lungs and interferes with breathing, causing shortness of breath, especially when a person is lying down. Heart failure also affects the ability of the kidneys to dispose of sodium and water. The retained water increases the edema.

CHF is the most common heart disease in the United States and it is estimated that over 5 million patients suffer from it. One of the more predictive hemodynamic parameters being measured in patients with CHF is blood pressure in the left atrium 410, e.g. left atrial (LA) pressure. To date, this parameter is measured by employing invasive right heart catheterization with a special balloon catheter such as the Swan-Gantz catheter.

Accordingly, in moderating for effects of CHF, it is desireable to measure the blood pressure in a particular chamber (either right atrium 415, right ventricle 419, left atrium 410 or left ventricle 420) in the heart 400 utilizing the telemetric medical system 30 according to the present invention.

Accordingly, in conducting one preferred method according the present invention, blood pressure can be directly monitored in the left atrium 410 of the heart 400. Accordingly, it is desireable to implant the sensor 50 at fossa ovalis 407 within the septum 405.

With respect to the specific anatomy of the septum 405, in approximately 15% of the normal population, the fossa ovalis 407 has a pre-existing hole or opening that either remains open or patent and is normally covered by a small flap of tissue. In approximately 85% of the normal population, the fossa ovalis 407 is completely occluded, e.g. there is no hole in the septum 405.

(1) Transcatheter Approach

In accordance with the method according to the present invention, a transcatheter approach has been found to be particularly useful for the patient population already having the pre-existing hole at the fossa ovalis 407. Accordingly, in performing this method according to the present invention, first, a transesophageal ultrasonic probe (not shown) is inserted into the patient's mouth and placed in the esophagus. In most cases, the transesophageal ultrasonic probe is positioned approximately 30–35 cm from the mouth, i.e. in most cases positioned just above the patient's stomach.

Under transesophageal ultrasonic guidance, a wire (not shown) is inserted into the right atrium 415 through an appropriate vessel such as the inferior vena cava 408 wherein the wire is guided through the fossa ovalis 407 by gently lifting the tissue flap away from the patent opening at the fossa ovalis 407. Once the wire is inserted through the fossa ovalis 407, the wire is guided to one of the pulmonary veins 416 for placement of the distal end of the wire in order to properly position and anchor the wire in the opening of the pulmonary vein 416. Accordingly, the pulmonary vein 416 has been proven to be a very reliable and steady anchoring point for the wire.

Once the wire is properly positioned in the fossa ovalis 407 and anchored in the pulmonary vein 416, a catheter sheath ("over-the-wire" type—not shown) is guided over the wire through the right atrium 415 and the fossa ovalis 407 and positioned within the left atrium 410, for instance, very close to the opening of the pulmonary vein 416.

Once the catheter sheath has been properly positioned, the wire is removed from the patient's heart 400 and the sensor 50 is delivered through the catheter sheath by one of the many standard catheter-based delivery devices (not shown). Accordingly, the sensor 50 can be delivered to the fossa ovalis 407 by any of the typical catheter-based delivery devices normally associated with implantable pacemakers, electrodes, atrial septal defect (ASD) occlusion devices, etc. Accordingly, the sensor 50 is deliverable with typical delivery devices such as the Amplatzer® Delivery System, manufactured by AGA Medical Corporation of Golden Valley, Minn.

Figure 11:
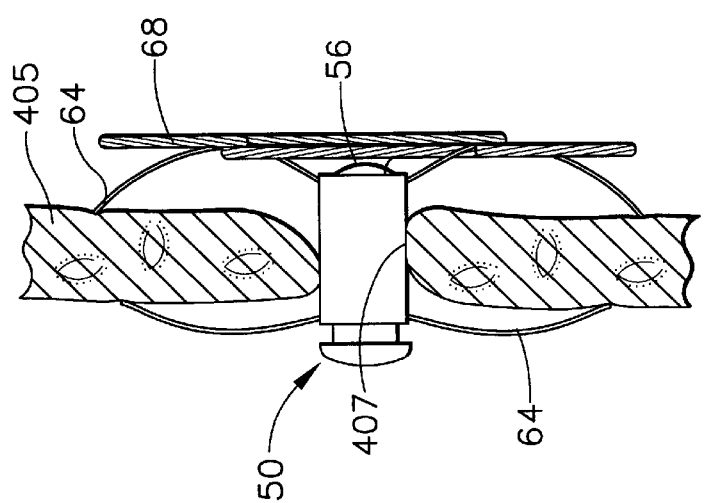
FIG. 11 is a schematic illustration depicting the sensor fully deployed within a tissue aperture according to the present invention.

After placement of the catheter sheath, the sensor 50 is deployed from the catheter sheath within the fossa ovalis 407 as best illustrated in FIG. 11. Upon deployment, the sensor 50 utilizes the anchoring legs 64 for anchoring the sensor 50 to the septum 405 and occluding the opening at the fossa ovalis 407.

(2) Anterograde Approach

The sensor 50 is placed in the fossa ovalis 407 for those patients not having a pre-existing opening in the fossa ovalis 407 through means of an anterograde approach. Once again, a transesophageal ultrasonic probe is positioned in the patient's esophagus as described above. Under transesophageal ultrasonic imaging guidance, an opening is made in the septum 405 at the fossa ovalis 407 in order to place and accommodate the sensor 50. Thus, the opening is made with a standard needle catheter (not shown) such as the BRK™ Series Transseptal Needle manufactured by St. Jude Medical, Inc. of St. Paul, Minn. Accordingly, under transesophageal ultrasonic guidance, the needle catheter is initially placed in the right atrium 415 and positioned at the fossa ovalis 407. At this point, the tip of the needle of the needle catheter penetrates the fossa ovalis 407 and the catheter is inserted through the fossa ovalis 407 into the left atrium 410 through the newly created opening in the fossa ovalis 407 by the needle catheter. Once the opening in the fossa ovalis 407 is created, the sensor 50 is introduced with the delivery device, such as the delivery device described above, and placed in the fossa ovalis opening as shown in FIG. 11. Upon deployment of the anchoring legs 64, the opening in the fossa ovalis 407 is occluded around the sensor housing 52 and the sensor 50 fixed to the septum 405 in a secure fashion.

It is important to note that transesophageal ultrasonic imaging is utilized for both the transcatheter and the anterograde approach as described above in accordance with each method step of the present invention. Since either method according to the present invention can be utilized with the transesophageal ultrasonic guidance, other imaging modalities such as flouroscopy can be eliminated. As such, the methods according to the present invention can be conducted in an outpatient clinic or doctor's office as a bedside procedure. By eliminating the need for a flouroscope, the method according to the present invention also eliminates the need for conducting the procedure in a catheter lab which only adds additional time and cost to the procedure and additional time and inconvenience to the patient.

After the sensor 50 has been implanted in the patient's septum 405, the patient is provided with standard treatment to prevent excessive coagulation or endothelialization. For instance, it is common practice to prescribe aspirin and/or an anticoagulant such as Heparin for a period of time such as six months.

With either of the methods described above, the sensor 50 is fixed to the septum 405 in order to provide real time pressure monitoring in the left atrium 410. Since the sensor 50 is a wireless transponder and a battery low power receiver, the sensor 50 does not impede the natural function of the heart 400 and is truly minimally invasive.

By utilizing the signal reading and charging device 140 at the exterior of the patient's body, continuous pressure readings are obtainable for both the mean and pulsating values of pressure in the left atrium 410 provided by the sensor 50.

With the telemetric system 30, the signal reading and charging device 140 maintains an active reading volume around the sensor 50 ranging anywhere from 5–25 cm, and preferably, an active reading volume ranging approximately 10–15 cm. Moreover, with the sensor 50, and the signal reading and charging device 140, it is possible to sample multiple readings per second. Preferably, approximately 10–20 readings per second are possible with the present invention.

Other attributes associated with the present invention when utilized as a pressure monitor in a chamber of the heart include monitoring a pressure range of plus/minus 30 mmHg; and accuracy (at five Mmsec. integration) of plus/minus 1 mmHg and a repeatability (at 5 msec. integration) of plus/minus 1 mmHg.

Although preferred embodiments are described hereinabove with reference to a medical system, devices, components and methods of use, it will be understood that the principles of the present invention may be used in other types of objects as well. The preferred embodiments are cited by way of example, and the full scope of the invention is limited only by the claims.

What is claimed is:

1. A telemetric medical sensor for implantation in a patient's body for measuring a parameter therein, the sensor comprising:
   a housing;
   a membrane at one end of the housing, the membrane being deformable in response to the parameter;
   a microchip positioned within the housing and operatively communicating with the membrane for transmitting a signal indicative of the parameter, wherein the signal is a digital signal, the microchip comprising an array of photoelectric cells;
   an LED for transmitting light at the photoelectric cells; and
   a shutter connected to the membrane and moveable between the photoelectric cells and the LED in response to deforming of the membrane.

2. The sensor of claim 1, wherein the photoelectric cells are arranged in staggered rows.

3. The sensor of claim 2, wherein the array includes a reference photoelectric cell.

4. The sensor of claim 3, wherein the reference photoelectric cell is not blocked by the shutter.

5. The sensor of claim 4, wherein the microchip further comprises a plurality of comparators operatively connected to the photoelectric cells.

6. The sensor of claim 5, wherein the microchip further comprises a buffer operatively connected to the comparators for storing and transmitting the digital signal.

7. The sensor of claim 1, wherein the sensor further comprises an antenna operatively connected to the microchip.

8. The sensor of claim 7, wherein the antenna is located at the exterior of the housing.

9. The sensor of claim 7, wherein the sensor further comprises a plurality of anchoring legs resiliently attached to the housing for anchoring the sensor into tissue.

10. The sensor of claim 7, wherein the housing includes a notch in an outer surface thereon.

11. The sensor of claim 10, wherein the housing further includes a circumferential groove at the notch.

12. The sensor of claim 7, wherein the housing further includes a tapered end.

13. The sensor of claim 12, wherein the tapered end includes a piercing tip thereon.

14. The sensor of claim 13, wherein the tapered end further includes helical threads thereon.

15. The sensor of claim 7, wherein the antenna is made of wire.

16. The sensor of claim 15, wherein the wire comprises silver and platinum iridium.

17. The sensor of claim 16, wherein the antenna has 20–25 turns.

* * * * *